United States Patent [19]

Kulick

[11] Patent Number: 5,423,804
[45] Date of Patent: Jun. 13, 1995

[54] PROCESS FOR TRANSECTING REMOTE CONSTRAINED SURGICAL LOCATIONS SUCH AS THE TRANSVERSE CARPAL LIGAMENT

[75] Inventor: Michael I. Kulick, San Francisco, Calif.

[73] Assignee: Laserscope, San Jose, Calif.

[21] Appl. No.: 197,447

[22] Filed: Feb. 16, 1994

Related U.S. Application Data

[63] Continuation of Ser. No. 989,740, Dec. 10, 1992, abandoned, which is a continuation of Ser. No. 646,947, Jan. 28, 1991, abandoned.

[51] Int. Cl.$^6$ .................... A61B 17/36; A61B 17/32
[52] U.S. Cl. ........................ 606/14; 606/15; 606/170
[58] Field of Search ............... 606/7, 13–17, 606/39, 170; 128/898

[56] References Cited

U.S. PATENT DOCUMENTS

| | | | |
|---|---|---|---|
| 4,249,533 | 2/1981 | Komiya | 606/15 |
| 4,564,180 | 1/1986 | Agee . | |
| 4,648,892 | 3/1987 | Kittrell et al. | 606/15 X |
| 4,747,405 | 5/1988 | Leckrone | 606/15 X |
| 4,834,729 | 5/1989 | Sjostrom . | |
| 4,842,578 | 6/1989 | Johnson et al. | 604/22 |
| 4,962,770 | 10/1990 | Agee et al. | 606/170 X |
| 4,963,147 | 10/1990 | Agee | 606/170 |
| 5,026,366 | 6/1991 | Leckrone | 606/7 |
| 5,029,573 | 7/1991 | Chow | 606/170 X |

FOREIGN PATENT DOCUMENTS

| | | | |
|---|---|---|---|
| 2639237 | 5/1990 | France | 606/15 |
| 2044104 | 10/1980 | United Kingdom | 606/15 |
| 8911832 | 12/1989 | WIPO | 606/16 |

OTHER PUBLICATIONS

3M Health Care Brochure, dated Oct. 1989 "Agee Inside Job Carpal Ligament Release System".
Sandzen, AFP, Nov. 1981, Carpal Tunnel Syndrome.
Smith, Arch, Phys, Med Rehabil. Sep. 1977, Carpal Tunnel Syndrome.
MacDonald, Journal of Hand Surgery, undated, portion of article on Carpal Tunnel Syndrome.
Yamaguchi, et al., Minnesota Medicine, Jan. 1965, Carpal Tunnel Syndrome.

*Primary Examiner*—Randall L. Green
*Assistant Examiner*—Mary Beth Jones
*Attorney, Agent, or Firm*—Banner, Birch, McKie & Beckett

[57] ABSTRACT

This invention relates to a process for incising the transverse carpal ligament in the hand for relief of the symptoms of carpal tunnel syndrome. More specifically, a process is disclosed in which incising energy, preferably laser energy, is introduced from under the ligament for transecting the transverse carpal ligament while permitting the surgeon to view the interface of transection. A probe, preferably attached to a pistol-type grip, includes at least one tube containing an optic viewing device (preferably fiber-optic), and a conduit for directing incising radiation for the ligament transection. The fiber-optic viewing device, energy conduit, and an optional suction tube commence at the pistol grip where they are connected to the requisite viewing device, energy source, and suction pump. The fiber-optic viewing device terminates at a sufficient distance from the pistol grip to permit extension from the insertion at the wrist to pass under the entire length of the transverse carpal ligament. The energy conduit terminates within the field of view of the fiber-optic viewing device for the discharge of ligament-transecting energy in the view of the fiber-optic device and preferably is maneuverable with respect to the probe itself. The protective device keeps vital structures away from the energy tip. The optional suction evacuates smoke and soot from the site of the surgery. An operative process is disclosed which includes the insertion of the probe into the wrist and transection of the transverse carpal ligament during visualization by the surgeon.

44 Claims, 8 Drawing Sheets

PROCESS FOR TRANSECTING REMOTE CONSTRAINED SURGICAL LOCATIONS SUCH AS THE TRANSVERSE CARPAL LIGAMENT

This application is a continuation of U.S. application Ser. No. 07/989,740 filed Dec. 10, 1992 abandoned, which is a continuation of Ser. No. 07/646,947, filed Jan. 28, 1991, abandoned.

This invention relates to a process for incising the transverse carpal ligament in the hand for relief of the symptoms of carpal tunnel syndrome. More specifically, a process is disclosed in which energy, preferably laser energy, is introduced from under the ligament for transecting the transverse carpal ligament.

BACKGROUND OF THE INVENTION

Carpal tunnel syndrome is a well established symptom complex resulting from median nerve compression at the wrist. Referring to FIGS. 1 and 2, the carpal tunnel T is located on the palmar aspect of the wrist (carpus or wrist bones) (see aspect of FIG. 1) between the distal wrist flexion crease 14 and, roughly, the center of the ulnar border of the thenar muscle mass 16. The anatomy of the carpal tunnel and its contents is shown in relation to the surface structures in the section of FIG. 2. The median nerve 20 is superficial on the radial aspect of the flexor tendons 24 and branches, just distally to the distal border of the transverse carpal ligament L. Those familiar with anatomy will know that four superficial flexors, four deep flexors, the flexor pollicis longus and the median nerve normally travel through this tunnel.

The boundaries of the carpal tunnel are inelastic on three sides (see bones B in FIG. 2). The dorsal radial and ulnar borders form the U-shaped configuration. The fourth side, palmar side is formed by the transverse carpal ligament.

Any condition, systemic or local, that reduces the normal available cross-sectional area of the carpal tunnel—either by increasing the volume of contents or by decreasing the diameter of the tunnel—causes local constriction of the median nerve (the structure most sensitive to compression in the tunnel). The most common symptoms are those of sensory abnormalities in the median nerve distribution of the hand. See M, FIG. 1. These include hyperesthesia (acute irritating hypersensitivity), paresthesia (burning, tingling "pins and needles" sensation), hypoesthesia (decreased sensitivity) and, occasionally, pain and numbness.

Surgery is indicated for long-standing cases of carpal tunnel syndrome refracting to consensitive care, especially those with obvious muscle atrophy of the median enervated thenar muscles, for relief of the symptoms. The purpose of the surgery is two-fold: (1) to release the pressure on the median nerve and (2) to diagnose and treat the pathology responsible for nerve compression.

SUMMARY OF THE PRIOR ART

Regarding the prior art, two surgical methods have heretofore been utilized.

The first of these methods is direct surgery on the hand. In the direct surgery technique, the skin is first incised. (See S on FIG. 1.) Thereafter, surgery through the subcutaneous tissue and the antebrachial fascia (a soft tissue layer lying between the subcutaneous and the transverse carpal ligament) is incised. Muscle may have to be divided to expose the entire ligament. With suitable clamping to expose the ligament, the ligament is isolated and transected. Thereafter, the incision is sutured closed. This process causes pain, post-surgical bleeding, and necessitates a considerable period of recuperation (usually period of up to three months growth). Finally, the incision to the hand is large and unsightly.

In U.S. Pat. No. 4,962,770 issued Oct. 16, 1990 to John M. Agee and Francis King entitled Surgical Method, an additional technique for carpal tunnel surgery has been described. In this technique, a longitudinal incision is made at the wrist. A substantially cylindrical surgical probe with an upwardly exposed viewing window is inserted from the base of the wrist into the palm underneath the transverse carpal ligament. The cylindrical probe includes a fiber-optic viewing device and a reciprocating knife. The knife moves, responding to a trigger on the probe, from a first retracted position within the probe to a second cutting position to the exterior of the probe where it protrudes from the upwardly exposed viewing window.

The probe is inserted so that the upwardly exposed viewing port extends beyond the transverse carpal ligament. A view is available during insertion. When a site for transecting the transverse carpal ligament is located, the trigger is pulled and the knife protrudes upwardly adjacent the ligament. When such protrusion occurs, view is obstructed. Retraction of the probe with the knife extended results in transection of the carpal ligament from underneath. Usually surgery includes a succession of probe insertions, raising of the knife and a cutting and pulling motion of the device to transect the transverse carpal ligament.

The shape of the ligament—which is not a flat plane —does not conform to the disclosed linear probe. Further, when activated, the blade cannot be observed for at least two reasons. First, it is never possible to see the cutting edge of a knife. Second, the physical mass of the blade blocks the view from the viewing device.

There is an additional disadvantage. There is no way that the surgical knife can be locally diverted to pass around local vital structure.

The process, using conventional surgery, includes bleeding with the resultant possibility of the generation of scar tissue. Such scar tissue can itself generate further construction within the carpal tunnel.

It is to be noted with the cutting knife as required in the '770 Agee Patent, the cutting tip of the knife can never be observed.

Laser surgery has been used previously in other body sites. Most commonly, and analogously with respect to this invention is laser surgery on various areas within the body, especially in the knee.

Regarding the differences between knee surgery and surgery of the hand, it will suffice to say that each is a completely different medical specialty defined by the radical differences between the surgical sites. The knee is a closed joint that is most commonly subject to loading with the weight of the body; the hand at the carpal tunnel is open at both ends of the tunnel and is not subject to loading of the bones defining the tunnel. In the enclosed knee, synovial fluid is present; in the carpal tunnel the site of the surgery is relatively "dry." In the hand around the carpal tunnel, the primary surgical target is the transverse carpal ligament with all adjacent structures—tendons, blood vessels, muscles, and especially nerves—constituting obstacles that must be avoided during the surgical procedure. The knee is a joint to which access can be provided from many different aspects; the carpal tunnel is a confined tunnel structure to which access can only occur in the narrow confines of the tunnel, already crowded with tendons, nerves, blood vessels and muscle.

Surgery at other sites in the body, especially the knee, has the further advantage of allowing proximal manipulation of the operating instrument. That is to say, the surgeon can externally manipulate the device to move the operative end of the device within the patient to move to an internal operating position. An example of such an instrument is a laparoscope, an instrument utilized in operations on the abdomen, and in particular, the stomach.

Typically, the laparoscope is a multichannel instrument carrying a fiber probe for discharging surgical energy and an optical viewing fiber. Additionally, it is common with such devices to provide for suction, irrigation, and a tube for the insertion and removal of various tissue-grasping devices.

In a laparoscope, the energy-discharging fiber at the end of the probe can be moved within the field of view provided by the optic fiber. The energy-discharging fiber is arrayed parallel to the longitudinal axis of the probe. At the tip of the probe, there is defined a fiber end holding section of the probe which raises and lowers with respect to the elongate axis of the probe.

In surgery, the physician first points the entire probe in the direction of the surgical site. The surrounding anatomy of the patient is conformable; it elastically permits the probe to be moved relative to the patient until the operative tip is near the surgical site. Thereafter, and when the probe is adjacent the surgical site, the surgeon raises or lowers the fiber end holding a section of the laparoscope at the angle necessary to direct the surgical energy discharged from the tip of the fiber. Thereafter, the entire probe is rotated to direct the energy-discharging fiber to the correct angle relative to the axis of the probe for the surgery.

The reader will understand that the above-mentioned surgical techniques for other parts of the body are not applicable to carpal tunnel surgery. Proximal manipulation of an elongate probe within the carpal tunnel at the wrist and hand is severely constrained.

It will further be understood that surgery utilizing ligament-transecting energy, such as laser energy, has not heretofore been attempted in the carpal tunnel.

SUMMARY OF THE INVENTION

A process is disclosed for transecting the transverse carpal ligament for surgical relief of carpal tunnel syndrome. A multichannel probe, preferably attached to a pistol-type grip, includes at least one tube containing an optic viewing device (preferably fiber-optic), and a conduit for directing incising radiation for the ligament transection. Preferably, the conduit for directing the incising radiation is a fiber for receiving and directing lased light; cutting is performed so that the actual cutting interface can be observed during the incision. Other forms of energy can be used, such as microwave radiation, ultrasound, or intensive heat from an electrical resistance element so long as cutting is present. Optimally, a suction conduit for receiving and withdrawing smoke and soot from the surgical site can be provided. Irrigation can also be provided.

Regarding the energy utilized for the transection, it is preferred that the energy source transect the ligament while at the same time applying cautery to any blood vessels transected in the surgery. This retards the post surgical development of scar tissue caused by bleeding within the carpal tunnel and mitigates the risk of such post operative tissue itself becoming a source subsequent of pressure on the median nerve.

The fiber-optic viewing device, energy conduit, protection device, and suction tube can commence at a pistol grip where they are connected to the requisite viewing/light device, energy source, suction pump and/or irrigation device. The fiber-optic viewing device terminates at a sufficient distance from the pistol grip to permit the visualization of transverse carpal ligament. The energy conduit terminates within the field of view of the fiber-optic viewing device for the discharge of ligament-transecting energy. Preferably the energy conduit is maneuverable with respect to the probe itself. For example, the tube containing an optical fiber for conducting lasing energy can be arcuate at the viewing end of the fiber-optic viewing device with the fiber having in-and-out motion with respect to the tube; alternatively, provision can be made for maneuvering the fiber in side-to-side and up-and-down motion by imparting to a semirigid fiber-carrying tube flexing tensile members in the side walls of the tube. Preferably, the suction tube is distal to both the fiber-optic viewing device and the energy-discharging conduit for the evacuation of both smoke and soot from the field of view of the laser surgery cutting site.

In the disclosed operation process, anesthesia is provided and a longitudinal incision is made at the distal volar forearm. A probe is inserted to create a tunnel for the probe of the instrument. The probe is inserted underneath the transverse carpal ligament, and the ligament visualized for its entire span. The suction is turned on, preferably by a control at the handle, the shield is activated, preferably by a control at the handle, and transection is commenced by the discharge of energy from the conduit as the probe is withdrawn from its insertion with the suction drawing the debris, obstructing fluids, smoke and soot, from the surgery out of the field of view of the fiber-optic viewing device. When the transverse carpal ligament is transected, the longitudinal incision sutured closed and the hand placed in a post surgical splint for recovery.

Provision is preferably made for a shield at the surgical site. The shield has two functions. First, the shield is deployed for preventing migration of the surrounding anatomy to the surgical site where the carpal ligament is being transected. Secondly, the shield can provide protection from the ambient radiation.

According to one aspect of this invention, a shield comprising a collapsible protective basket is disclosed. The collapsible wire basket is located on the outside of the probe near the active portion of the energy tip. It is attached to the probe at one end and to a reciprocating portion on the probe at the other end, and is moveable between and expanded disposition with respect to the probe and a collapsed disposition with respect to the probe.

In the expanded position, the basket displaces outward in a hemispherical configuration. Outside of the basket, the contents of the carpal tunnel are screened from the surgical site. Further, the contents of the carpal tunnel are held at a distance with respect to the carpal tunnel so that radiation from the surgery does not appreciably affect this tissue. Inside of the basket and in the portion of the probe above the basket, surgery occurs.

It is to be noted, that expansion of the basket to protect the surgical site prevents the exterior of the probe from being rotated. This being the case, it is necessary that the energy fiber be capable of full manipulation distally with respect to the end of the probe. It is not possible—with the basket deployed—to first position the energy-discharging tip of the fiber with respect to the probe and thereafter to rotate the entire probe along its axis to reach the surgical site.

In another embodiment of the disclosed shield, an inflatable surgical balloon is disclosed. During insertion, this balloon resides adjacent to the probe—preferably in a cavity defined in a side wall of the probe. When the probe is used during surgery, the balloon is expanded. In the inflated position, the balloon typically expands below the surgical site. The balloon has the advantage of being made of a material that is opaque to the surgical energy being utilized for the transection. Consequently, the balloon can provide radiation shielding of the surrounding tissue from the surgical site.

An advantage of the disclosed surgical instrument and procedure is that surgery of the skin, subcutaneous tissue, and antebrachial fascia is not required for access to the transverse carpal ligament.

A further advantage of the disclosed surgical procedure and instrument is that transection occurs in full view of the physician utilizing the fiber-optic viewing device. In short, the cut is not "blind." A view of the cutting interface is provided at all times. As distinguished from the use of a scalpel—or other surgical knife—the actual cut interface itself is visible to the surgeon.

Yet an additional advantage is that transection occurs from the carpal tunnel palmarly. Cutting is away from the median nerve and other structures that could be damaged.

An additional advantage of the disclosed operation process is that a suction for fluid, smoke, and soot from the site of the surgery is provided. This suction can be combined with irrigation. There results a clear view of the surgical site.

An additional object of this invention is to provide for maneuvering of the lasing fiber in the field of view of the fiber-optic viewing device. According to this aspect of the invention, the conduit discharging the transecting surgical energy is encased within a conduit at the end of the probe that can be remotely steered. For example, the conduit can be a tube bent with an arcuate configuration at the end permitting in-and-out movement of a fiber conducting lasing energy. Alternatively, the conduit can have a semirigid exterior which is flexed by tensile members on the conduit exterior for steering the conduit up and down and side to side relative to the end of the probe.

An advantage of this aspect of the invention is that moving the probe within the surgical tunnel in the arm of the patient is minimized. Gross manipulation of the probe does not have to occur to direct the incision; instead the incision is directed remotely, relative to the end of the probe.

An advantage of this aspect of the invention is that proximal manipulation of the probe is not practical within the carpal tunnel confines. Consequently, once the probe is inserted, manipulation of the probe with respect to the tunnel and contents is held to a minimum and providing for a change in direction of cutting not attainable by altering the position of the probe via extended manipulation due to the confined space.

An additional object of this invention is to provide a shield at the site of the surgery disposed downward to and toward the carpal tunnel. According to one aspect, a collapsible peripheral protective basket is disposed axially of the probe. When the probe is inserted, the basket is collapsed; when transecting surgery occurs, the basket is expanded around the surgical site.

An advantage of this aspect of the invention is that the contents of the carpal tunnel are screened off from the site of the surgery. Thus, nerves, blood vessels, and other structures that might inadvertently find access to the surgical site are effectively screened off. A safer surgery results.

According to an alternate embodiment of the invention, a balloon expands from the probe. The balloon is opaque to the radiation emitted. The dual function of screening off both radiation and portions of the anatomy that stray to the site of the surgery can be realized.

An advantage of the full manipulation of the surgical energy-discharging fiber is that when the basket, balloon, or other shielding device is deployed from the end of the probe, rotation of the probe within the narrow confines of the carpal tunnel is constrained. Nevertheless, the full motion of the optical fiber here disclosed enables surgery to continue.

BRIEF DESCRIPTION OF THE DRAWINGS

Other objects, features and advantages of this invention will become more apparent after referring to the following specification and drawings in which.

DESCRIPTION OF THE PREFERRED EMBODIMENT

Figure 3:
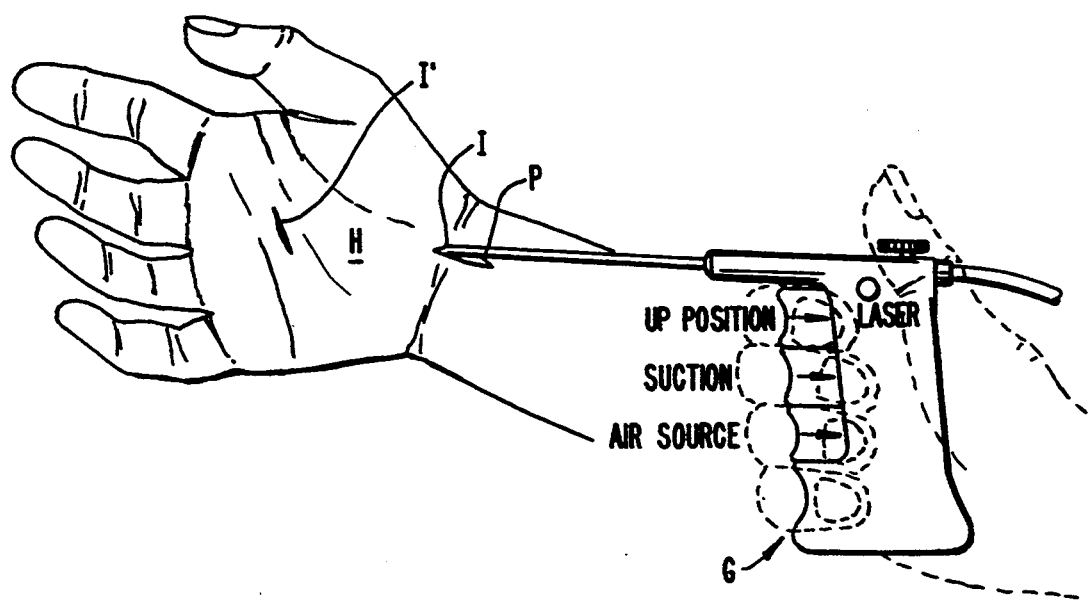
FIG. 3 is a perspective view of the probe of this invention attached to a pistol grip.

Referring to FIG. 3, a pistol grip G having a protruding probe P is illustrated. The probe P is being placed within a longitudinal incision within hand H. Insertion occurs through a longitudinal incision I at the distal polar of the forearm at the base of hand H. An alternate incision for insertion of the probe is shown at I'.

The gross manipulation of the disclosed surgical instrument having been described, its operative portions can be set forth.

Figure 4A:
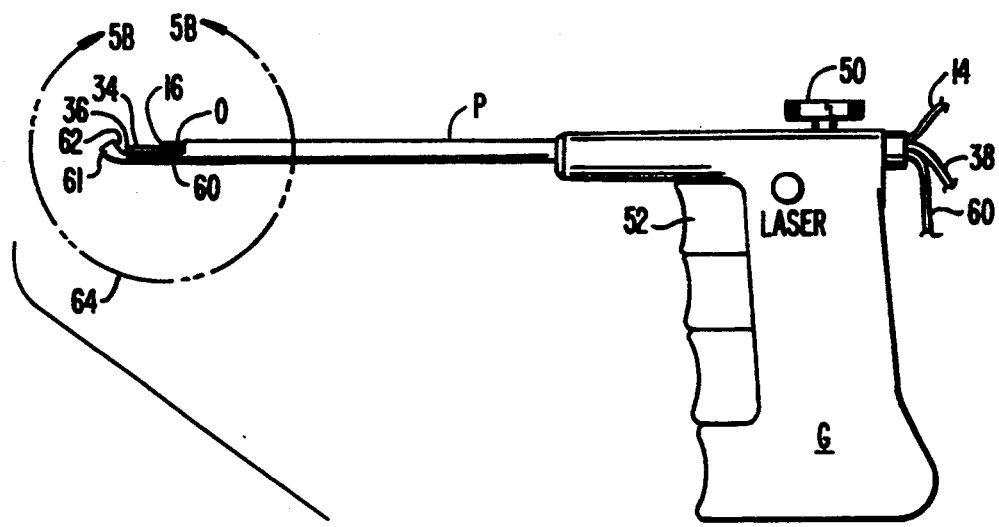
FIG. 4A is a side elevation of the disclosed probe with connection being shown to remote viewing, lasing and suction devices.

Referring to FIG. 4A, a pistol grip G is illustrated with probe P protruding from the "gun barrel" position relative to the grip. It will be understood that since the subject of this invention relates to surgery in small and confined places, the probe is made as small as practicable. Further, the probe—and all its contents—can be semirigid. That is to say, the stiffness of the probe is sufficient to permit insertion; but flexible enough to accommodate blunt dissection at the tip of the probe so that the probe P finds its way between anatomy structures without incising them. This being the case, the reader will understand that the drawings illustrating the best mode of this invention contemplated at this time are not necessarily to scale; such dimension may be added by the routineer.

Two conduits are required for probe P. The first conduit is for an optical viewing device O. Optical viewing device O can have any standard configuration. Preferably it comprises an optical fiber 14 having a wide-angle lens 16 at the end. The optical fiber is connected to a viewing device 20, which viewing device can either be an eyepiece or a monitor for displaying the field of view seen at lens 16. I contemplate other viewing devices including remote and miniature video cameras.

Secondly, the probe must include a conduit 38 for transmitting energy sufficient for transection of the transverse carpal ligament. Conduit 38 terminates at end 34 where the energy within the conduit is discharged from tip 36 at the surgical site. This discharge must occur within the field of view of the lens 16 so that transection occurs within the view of the surgeon.

In the embodiment here shown, an optical fiber 38 connects to a laser power source including a laser amplifier. The optical fiber is capable of in-and-out motion with respect to conduit 30; thus the fiber is maneuverable with respect to the probe P. For example, I have constructed the probe from a hypodermic needle having a bent end; an optical fiber was moved with an "in and out" motion with respect to the hypodermic needle. An optical fiber viewing device was taped to the needle. The device was sufficient for surgery related to the transection of the transverse carpal ligament, a procedure which I, for the first time, performed.

Figure 5B:
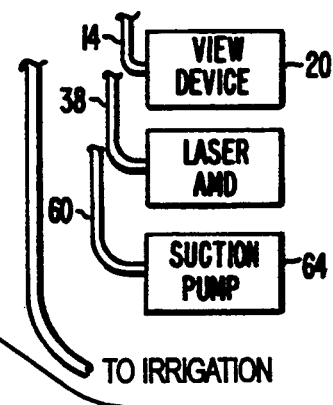
FIGS. 5A, 5B and 5C are respective perspective, side elevation and plan views of the tip of the probe illustrating the relationship of the suction device distally from the end of the probe for the withdrawal of smoke and soot from the surgical site and away from the view of the fiber-optic device and the surgical procedure at the energy discharging conduit.
Figure 5B:
Figure 5C:
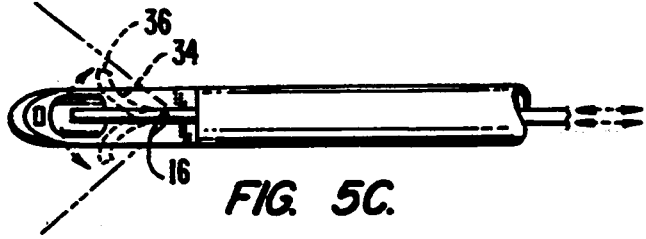
Figure 4B:
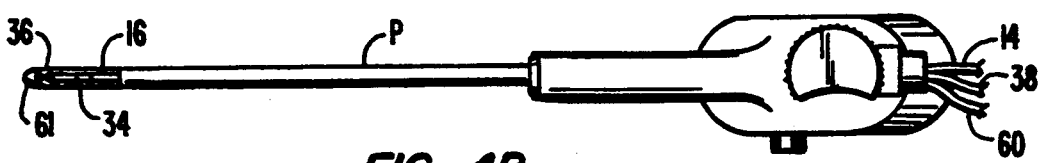
FIG. 4B is a plan view of the disclosed probe shown in FIG. 4A.
Figure 5A:
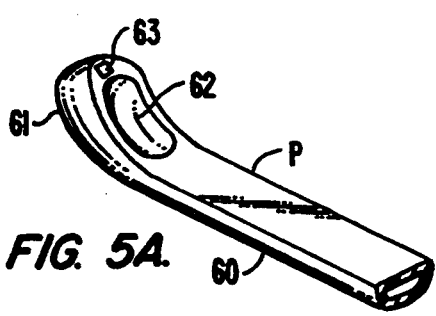

Referring to FIG. 5A, I illustrated the probe P at the blunt dissector end 61 of the probe. It will be seen that the opening 62 of the probe P defines a suction entrance volume 62, this volume having multiple purposes. First, and most apparently, it draws the smoke and soot of surgery away from the view between lens 16 and tip 36. Secondly, and as the probe advances, it defines an upwardly exposed cavity in which the disclosed surgery can occur. Finally, and at pad 63, a relative hard spot is defined at the tip of the probe P whereby structure can be impressed (felt) with the probe P.

I contemplate construction of the probe from molded, semirigid construction materials such as those selected from plastics commonly used in surgery. Naturally, other materials will suffice.

Referring to FIGS. 5B and 5C, I disclose a conduit 30 having an optical fiber which is maneuverable with respect to the end of probe P. Specifically, the motion here illustrated is side-to-side and up-and-down motion. Such motion is well known. By way of example, endoscopes commonly accommodate such motion at their tips. An illustration of such an endoscope is Nasal Endoscope manufactured by the Makatsu Corporation of Tokyo, Japan. While this endoscope is larger than the fiber steering conduit I contemplate, this is a matter of scale.

Figure 6:
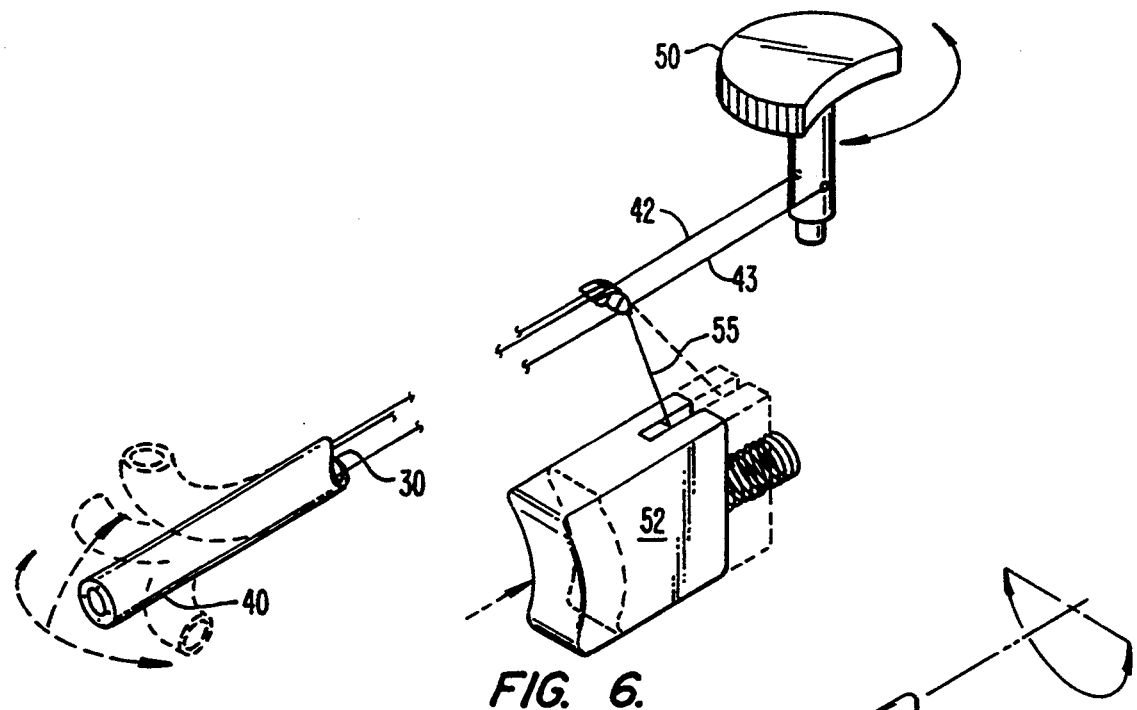
FIG. 6 is a perspective illustration of the operative energy discharging fiber encased within a directionally steerable outer sheath such as that found on endoscopes, with the control structure to the tip of the directionally steerable structure being schematically shown.

Referring to FIG. 6, the operation of steering function can be understood. Specifically, a semirigid end 40 is provided around conduit 30. Tensile elements 42, 43 are provided along the side walls of the semirigid end 40. As is well known, by providing differential tension on elements 42, 43, remote steering of probe P at the distal end can occur. I prefer to place wires 42, 43 to a knurled wheel 50 for the side-to-side direction of the optical fiber. Up-and-down motion can be directed by wire 55 connected in a similar manner to trigger 52 on grip G (not shown in FIG. 6.

In the preferred embodiment illustrated in FIG. 4A, I include a suction conduit 60 with an open end 61. As can be seen in the side elevation of FIG. 4A, open end 61 is distal to both the end of the fiber 36 and lens 16. Suction conduit 60 is connected to suction pump 64.

FIGS. 5B and 5C show respective plan and side elevations of the suction only. It can be seen that opening 62 and end 61 of suction conduit 60 is disposed immediately underneath end 36 of fiber 34. In this disposition, and during the surgery, smoke and soot that might obstruct the view of end 36 of fiber 34 are removed. The field of view from lens 16 is schematically shown.

Figure 7:
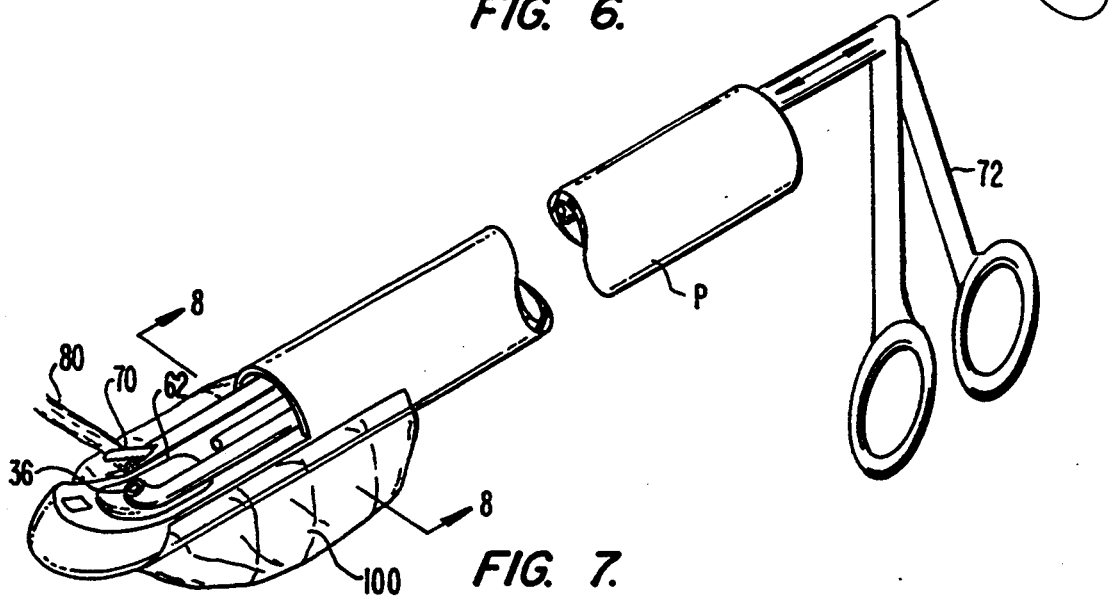
FIG. 7 is a perspective view of the semirigid probe illustrating the insertion of a grasping and manipulating surgical appliance in the combination of the disclosed probe, the schematic format here shown omitting the pistol type handle for ease of understanding, this illustration setting forth in perspective view a deployable shield in the form of an expansible balloon.
Figure 8:
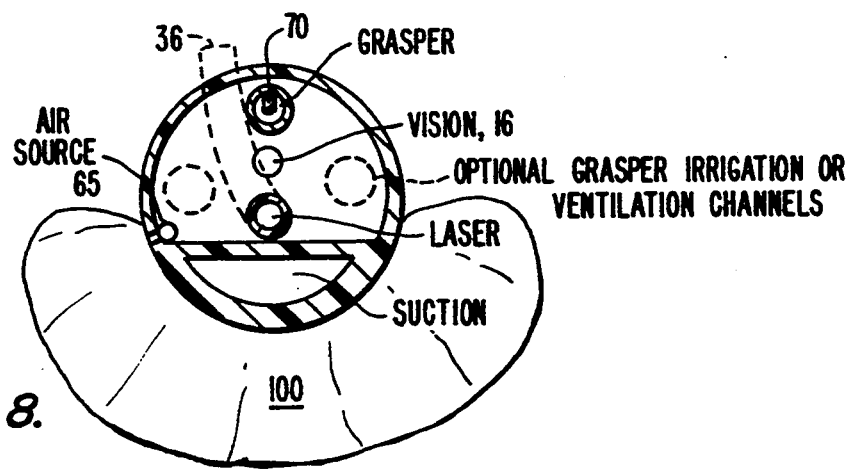
FIG. 8 is a side elevation section at the end of the probe along lines 8—8 of FIG. 7 illustrating the relative elevations of the appliance members and illustrating the balloon as an inflated structure for performing the micro surgery disclosed.

Referring to FIG. 7, I illustrate two additional features of my invention. First, I illustrate grasping devices utilized in combination with probe P. The surgical grasping device contemplated is manufactured by the Acuflex Corporation of Mansfield, Mass. This device includes to blunted, opposed jaws 70 at the tip with a scissors like handle 72, which scissors like handle 72 can be rotated remotely from the instrument. I choose not to illustrate the pistol grip G for ease of understanding. In the current embodiment, limited towards and away motion is provided by handle 72 as well as rotation.

It will be seen that in the schematic of FIG. 7, I illustrate a tissue member 80 being grasped, with tip 36 having just severed its outer portion with disposal to underlying suction entrance 62.

FIGS. 7, 8, 9A and 9B illustrate my instrument with an additional attachment.

Figure 9A:
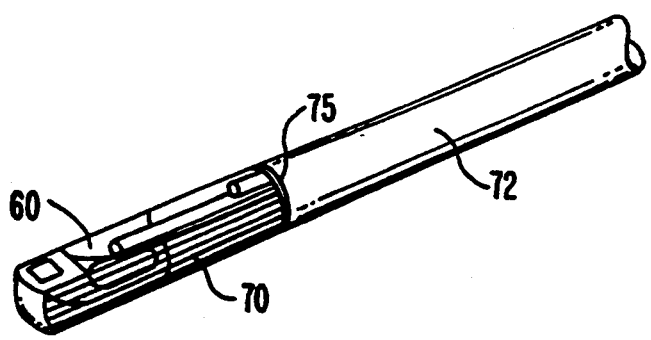
FIG. 9A is a perspective view of an alternate embodiment of the probe including a collapsible basket, the basket here being shown in the collapsed position on the exterior of the probe for insertion of the probe to the surgical site at the transverse carpal ligament.
Figure 9B:
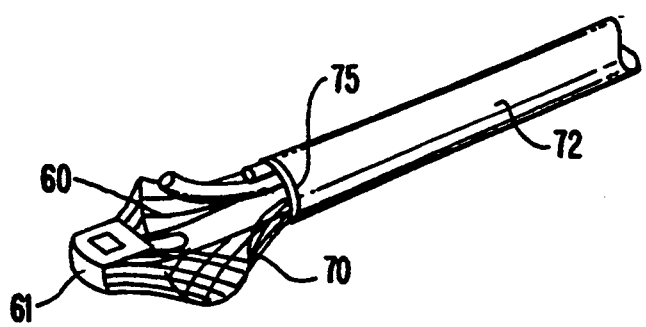
FIG. 9B is a perspective view of the alternate embodiment of the probe showing the collapsible basket expanded as it would be in the surgical site underneath the transverse carpal ligament for shielding tissue, such as nerves and blood vessels, from the site of the transection of the transverse carpal ligament.

Referring to FIGS. 9A and 9B, the exterior of the probe P is covered with a flexible mesh structure 70 attached to the tip of probe P. Flexible mesh structure 70 in the collapsed position illustrated in FIGS. 9A. Flexible mesh structure is attached at 75 to a sleeve 72 on probe P. Attachment to end 61 of probe P occurs as well.

To maintain the flexible mesh structure 70 in the closed position, sleeve 73 biases flexible mesh structure 70 away from the end of probe P. (See FIG. 9B).

Referring to FIG. 9B, opening of flexible mesh structure 70 on the end of probe P can be understood. Sleeve 73 is moved forwardly. Flexible mesh structure 70 expands away from the sides of probe P while remaining attached to the distal end of probe P.

It is important to observe that flexible mesh structure 70 only covers the bottom of the probe P below suction conduit 60 at end 61. That is to say, with respect to the longitudinal axis of probe P illustrated, only that portion of the probe P disposed away from the transverse carpal ligament is shielded, the shielding occurring for approximately 180° around the axis of probe P.

Figure 1:
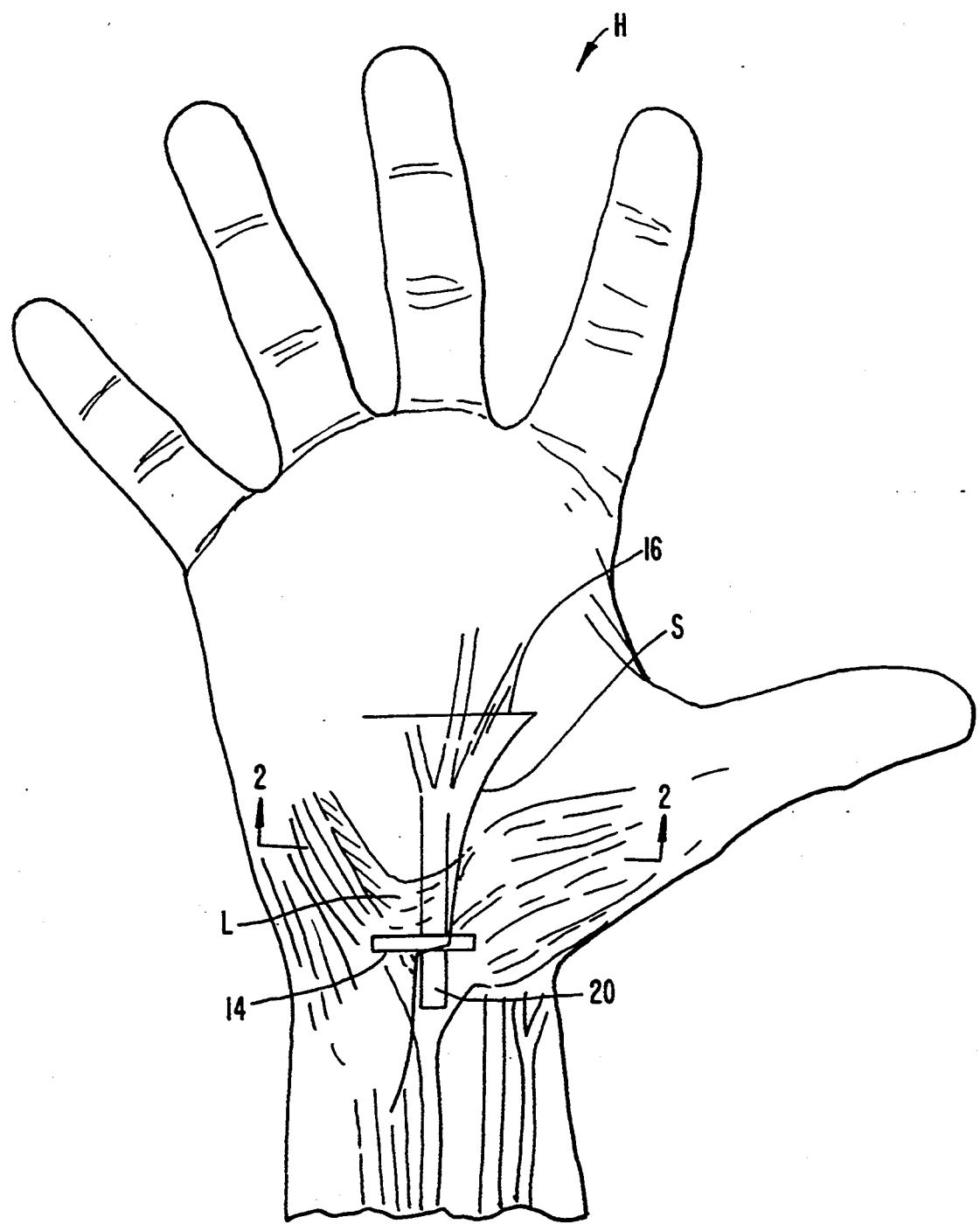
FIG. 1 is a palmar view of the a right hand with surgically important structures noted on the exterior of the hand.
Figure 2:
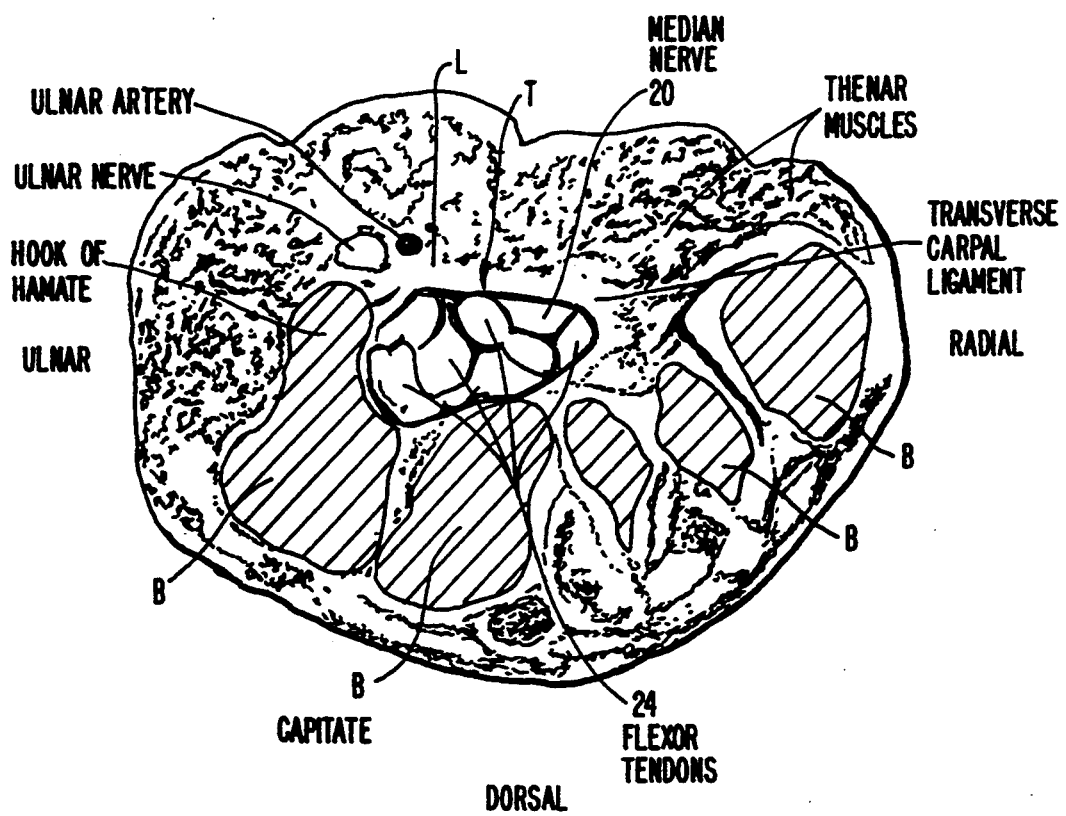
FIG. 2 is a cross section of the wrist at the level of the hook of the hamate illustrating the anatomy of the carpal tunnel and its contents.

The function of the flexible mesh structure 70 is easy to understand. Specifically, blood vessels and nerves (See FIG. 2) within the carpal tunnel are shielded and kept away from the transection surgical site.

Referring back to FIG. 8, it will be understood that the deployable shield that I contemplate can be a balloon 100. Typically, balloon 100 is fastened to the sides of the probe P, just below suction entrance 62. It extends around the bottom circumference of the probe—it does not extend over suction entrance 62. Inflation and deflation occurs through conduit 65. In this disposition, preferred protection in the format of a deployable shield is provided.

Figure 10A:
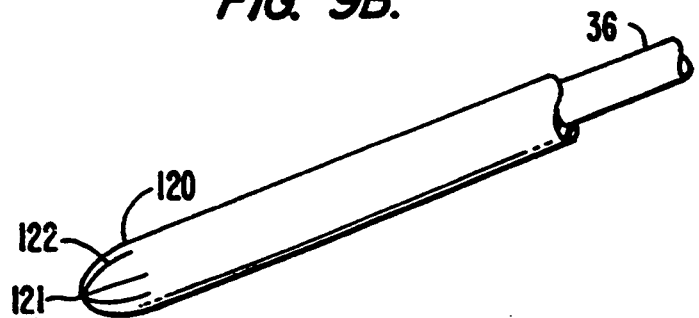
FIG. 10A is an illustration of a protective sheath in the collapsed position adjacent the energy discharging conduit for preventing sticking of the fiber of tissue and providing a self-cleaning action.
Figure 10B:
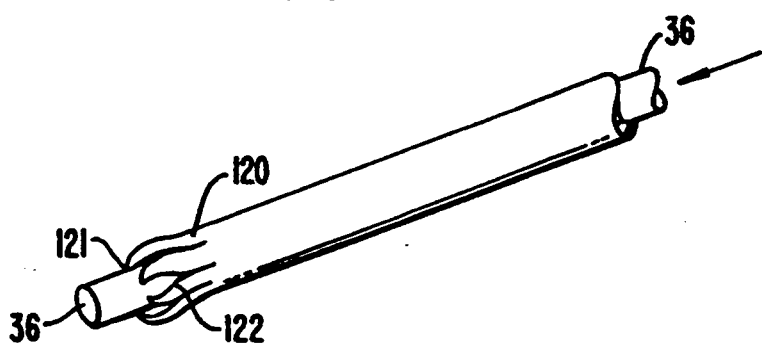
FIG. 10B is an illustration of the protective sheath shown in FIG. 10A in the expanded position.

Referring to FIGS. 10A and 10B, I contemplate a self cleaning and protective sheath 120 over fiber end 34 covering tip 36. Simply stated, controlled in and out motion (pistoning) is contemplated. Since tip 36 is in effect hot, tissue will adhere. Further, upon advance of the probe P, tip 36 could become impaled. This being the case I contemplate plastic cover 120 having spherical end 121 with serration 122. When the tip 36 is retracted, cleaning of the fiber end occurs. In the retracted position, advancement with reduced risk of impailment can occur. For use, fiber 34 is advanced out of sheath 122 opening spherical end 121 at serration 122.

Figure 11A:
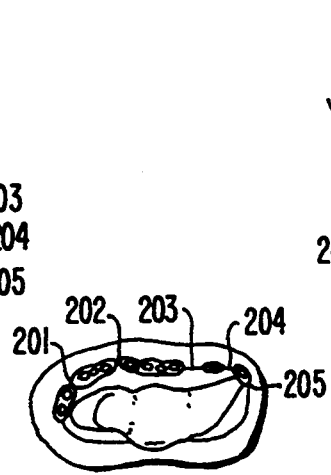
FIG. 11A is a section of the wrist.
Figure 11B:
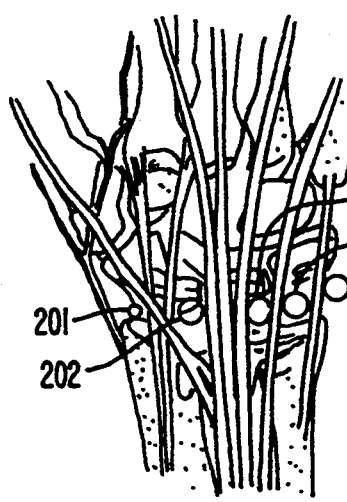
FIG. 11B is a section of the palmar side of the hand.

FIGS. 11A and 11B illustrate the wrist Joint and these are the portals of entry and there are six reference portals which you can insert my probe for the purpose of entering the Joint and treating problems within, inside the wrist.

In the cross-section the portals are labelled between the six sensor compartments in the back of the hand, named with 201–205 going from the radial side, which is the the thumb side, to the ulnar side, which is the little finger side. So, between the first and second extensor compartment are portals 201, between the third and fourth extensor compartment there is a portal 202, between the fourth and fifth extensor there is a portal 203, and on either side of the sixth extensor compartment is a portal 204, 205, the portal being a zone of entry. That is with the joint between the forearm bones and the wrist bones.

Now with respect to each one of those portals at the wrist, they basically meets my qualification if the surgical site is a joint and a probe is inserted to it, the probe, in reaching the surgical joint, is going to be constrained. Proximal manipulation of the probe in order to effect the movement of the distal end of the probe P for surgery is impracticable. Rather, it is going to be the movement at the distal end of the probe P that is going to do the surgery.

Figure 11C:
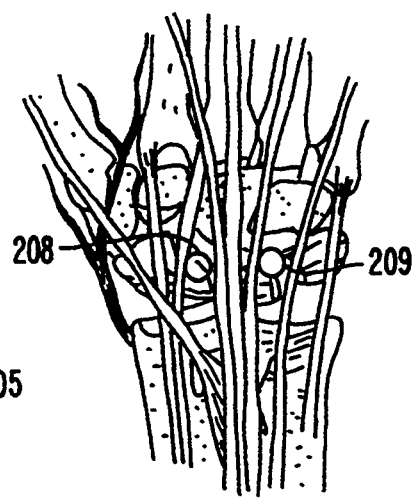
FIG. 11C is a section of the back side of the hand.

Referring to FIG. 11C, the Same thing holds true for the other wrist Joint, which is the midcarpal wrist joint, which is illustrated with respect to the back side of a hand. Two surgical portals 208, 209 for the midcarpal Joint. These particular portals are between the proximal and midcarpal bones interspaced between the extensor tendons as shown.

Figure 16:
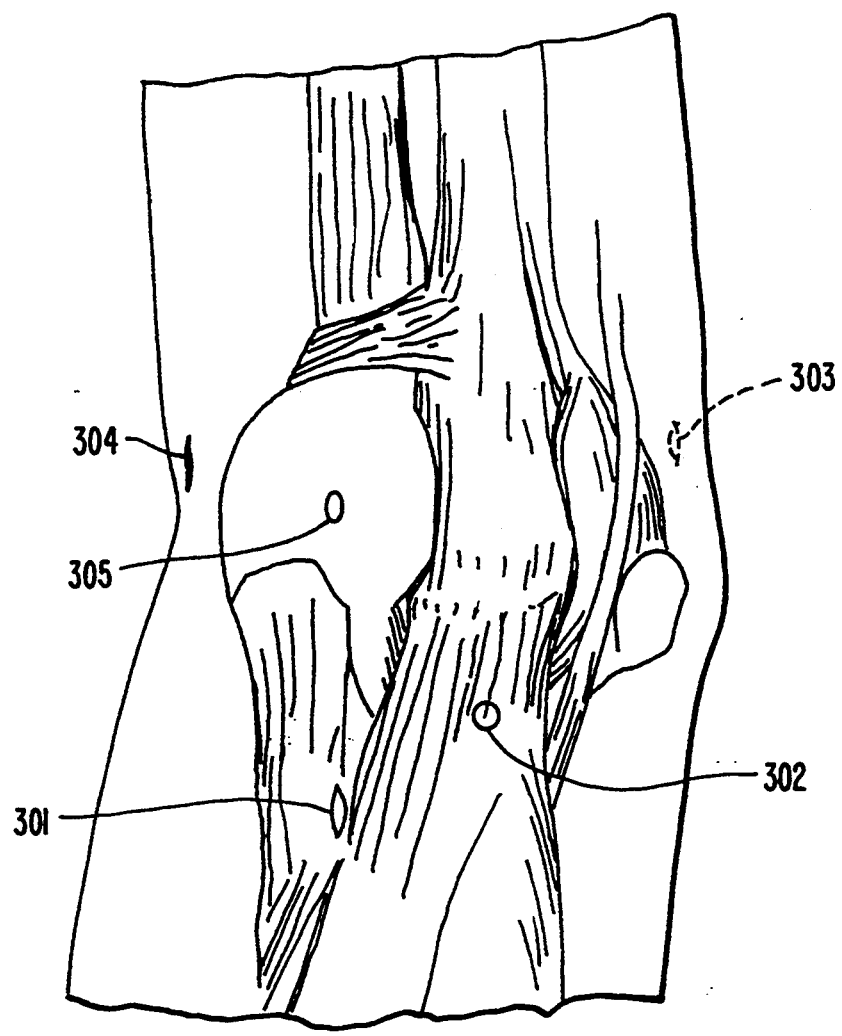
FIG. 16 is a schematic of the human elbow.

Referring to FIG. 16, the structure of the elbow is illustrated. The posterolateral portal 301, the straight posterior portal 302, the anteromedial portal 303, the anterolateral portal 304, and the straight lateral portal 305 are schematically shown. These portals, and the surgical sites underlying them, generally meet the qualifications that proximal movement of the probes to accomplish distal movement of the energy discharging fiber is not practical because of either the constraint of the surrounding tissue or possible damage to the surrounding anatomy.

And the reason that there are so many portals in the wrist, unlike the knee, is again because the knee permits proximal manipulation of the device to get to your operative site, whereas in the wrist you cannot really manipulate this proximally to get to all fields. That is why it is required to specify so many different, separate portals in this area of the human anatomy.

Figure 12A:
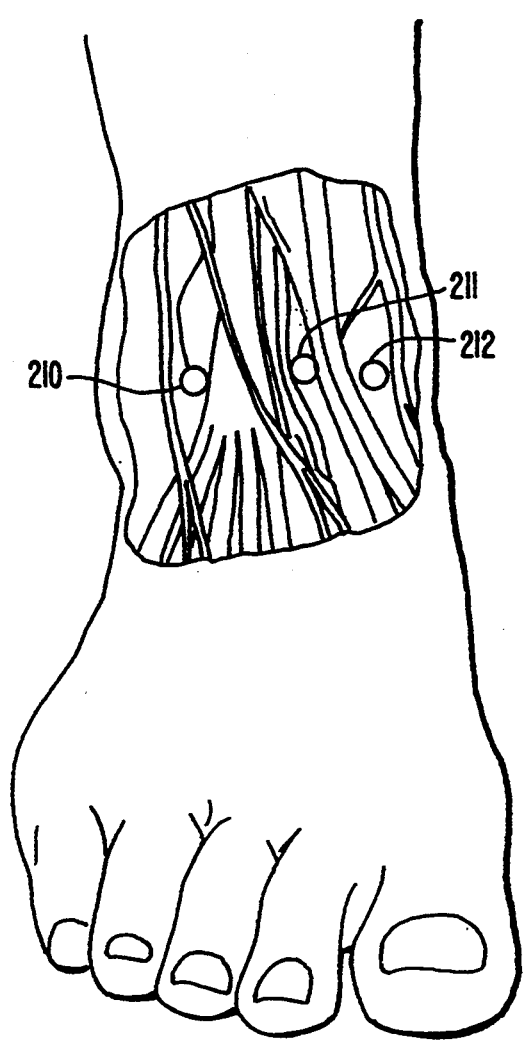
FIGS. 12A and 12B are respective illustrations of the anterior and posterior portions of a human foot.
Figure 12B:
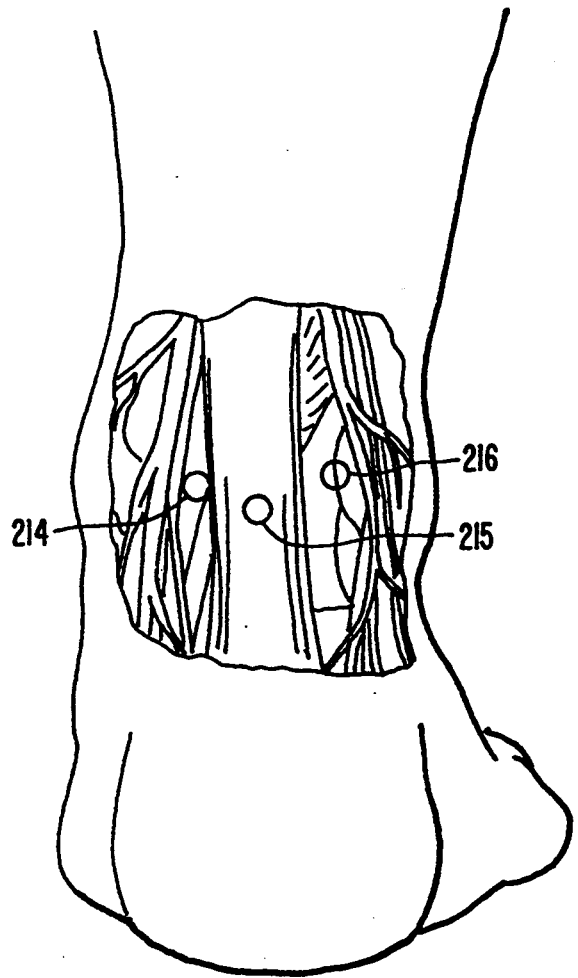

Regarding the portals of entry to the foot at the ankle, these again have the same problem. Referring to FIG. 12A, from the anterior aspect of the foot, which is the opposite side of that which is walked on, is illustrated coming toward the viewer. You walk on the plantar surface and the side that you put the scope in is either in the anterior (FIG. 12A or the posterior part (FIG. 12B), which is by the Achilles tendon. So, there are three anterior portals 210, 211, 213, and three posterior portals 214, 215, 216, being anterior lateral, anterior central, anterior medial posterior being posterior lateral, trans-Achilles (which means you go right through the Achilles tendon) and the posterior medial portal. Again, the problem here is that, the reason we have so many portals is because of the limited space in that point, unlike the knee, which means you cannot manipulate the instrument proximally in order to get the distal end of the probe to move for operative engagement within the surgical site. As I disclose with my preferred probe, all movement has to be in the operative sits at the distal end of the probe without concomitant movement of the proximal side.

Figure 13:
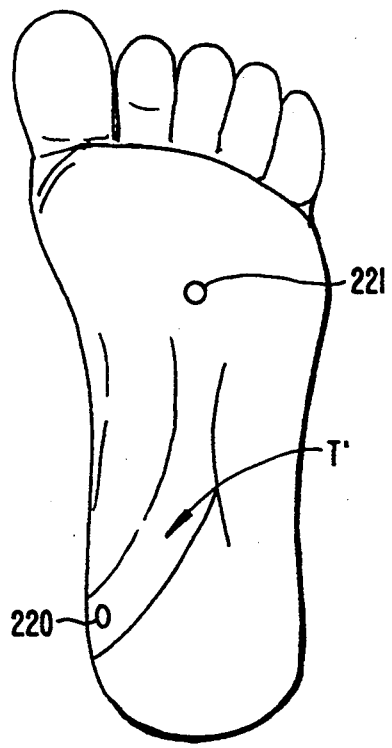
FIG. 13 is an illustration of the planar side of the foot to show the tarsal tunnel.

Referring to FIG. 13, the plantar side of the foot to demonstrate surgical ports of entry having the same constraints. It is to be noted that like in the hand in the hand where there is a carpal tunnel, in the foot there is tarsal tunnel T'. The tarsal tunnel is like the hand in the sense that there are tendons, nerves, and blood vessels going through a space, which has a fixed boundary on three sides, except for the fourth boundary, which is a ligament. That ligament basically is the soft structure. Anything that causes increase in content volume in that space will cause pressure on the structures within that space and the structure most sensitive to pressure is the nerve causing symptoms. Again, the disclosure herein sets forth a surgical probe instrument that is ideal for that because it permits transcotton of that tunnel without a fairly large incision on the bottom of the foot, which would take a long time to heal.

Entry occurs on either the plantar surface of the foot 221, or preferably the instep 220.

Figure 14:
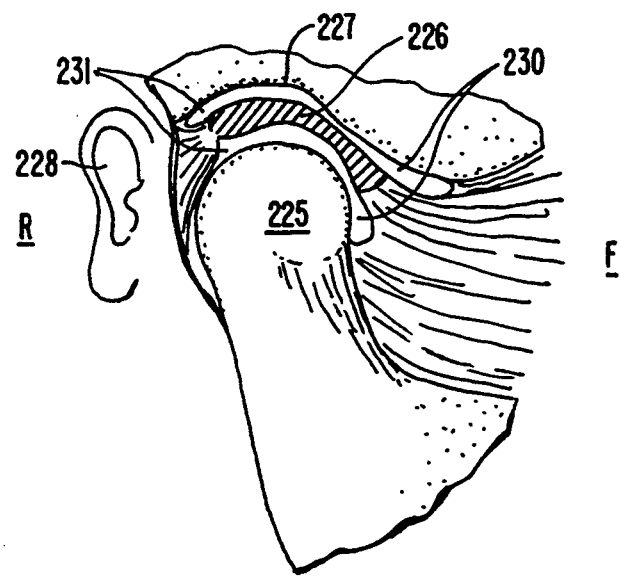
FIG. 14 is a section in the skull adjacent the mandibular joint.

Referring to FIG. 14, the temporomandibular joint is illustrated. That is the Joint in the Jaw where the mandible meets the cranium or the skull. The condyle 225 of the mandible; the articular disk 226; the cranial base 227; the ear canal 228; the front F of the person; the back R of the person. The points of entry are directly in front of the ear canal 231 or in front of the condyle. Potentially, there are four entry points.

Figure 15A:
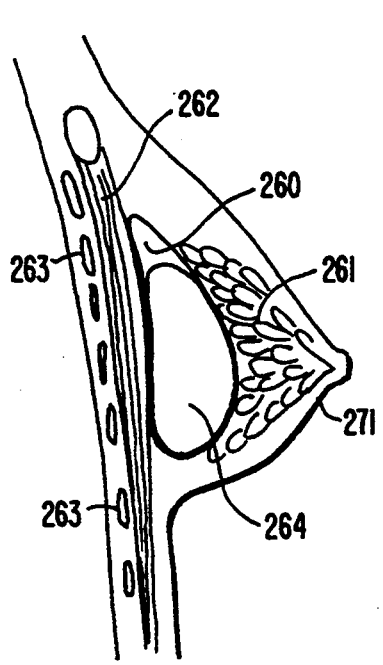
FIG. 15A is a representative illustration of a first position of female breast augmentation implants.
Figure 15B:
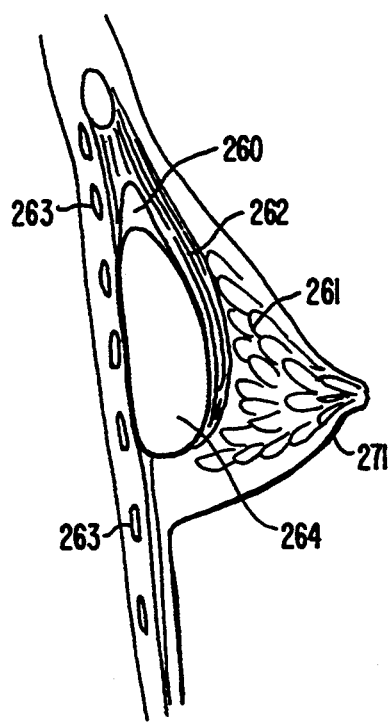
FIG. 15B is a representative illustration of a second position of female breast augmentation implants.
Figure 15C:
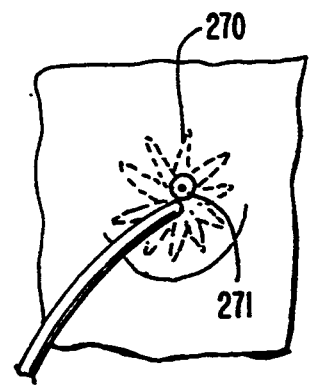
FIG. 15C is a schematic of a procedure preferably utilizing the semirigid probe of my invention.

Referring to FIG. 15A, 15B and 15C, a female breast is illustrated having an implant 264. The breast implant 264 is shown in 15A and 15B following breast augmentation. The implant is shown in FIG. 15A above the pectoralis muscle or below the pectoralis muscle. In either case, a capsule or scar tissue 260 forms around the implant 264.

In FIGS. 15A and 15B, implant 264 is shown within a scar tissue capsule surrounding the implant 264. Breast tissue 261, the pectoralis muscle 262, and the anterior rib cage 262 are also shown.

As is well known, the scar tissue of the capsule can either contract or shrink. The breast implant becomes hard. Nerves can either be directly affected by the scar tissue or alternatively the implant itself can pinch a nerve.

The way I treat this problem with my probe is by incising this capsule in a star pattern or cartwheel pattern, see FIG. 15C at 270, dividing the scar, allowing the implant to roam in a bigger pocket, the implant becomes softer again.

The probe P of my disclosure would enter either through the side (not shown) or through the areolaf area Just to get to the implant at the interface between the implant and the capsule. In such penetration, access to the scar tissue is desired; injury to the implant is to be avoided.

It will be appreciated that in such a procedure, my probe P will be particularly useful if it is of semirigid construction.

Presuming the skill and knowledge of a hand surgeon, the operation is easy to understand.

In the disclosed operation process, anesthesia is provided and a longitudinal incision I is made at the distal polar of the forearm (or wrist). Optimally, a solid probe having the overall dimension and cross section of probe P is inserted to create a temporary tunnel for the probe of the instrument. This typically occurs with a transitory compression of the median nerve 20 (See FIG. 2).

The probe P of the instrument is then inserted underneath the transverse carpal ligament T, and the ligament visualized for its entire span. The suction pump 64 is turned on and transection commenced by the discharge of energy from the optical fiber 34 at end 36. Appropriate in-and-out, side-to-side, and up-and-down movement of the fiber 34 at end 36 in conducted under the view of the surgeon through lens 16. During the discharge of the transecting energy, conduit 60 with the suction draws the smoke and soot of the laser surgery out of the field of view of the orthoscope. Surgical shield 70 is preferably deployed. When the transverse carpal ligament is transected, the probe is withdrawn, the longitudinal incision sutured closed and the hand placed in a post surgical splint for recovery.

It will be understood that I exclude surgery by knife from the contents of this disclosure. Further, I prefer to utilize laser energy. Laser energy ranges sufficient for the performance of the surgery set forth in this invention for the transection of the transverse carpal ligament are contained in U.S. Patent application Ser. No. 09/621,451, of Peter S. Hertzmann and Jordan K. Davis filed Nov. 30, 1990 and entitled A METHOD FOR PERFORMING PERCUTANEOUS DISKECTOMY USING A LASER. This application is a Continuation-In-Part of U.S. Pat. Ser. No. 07/463,759 filed Jan. 12, 1990. This application and especially its laser frequency ranges are incorporated to this disclosure by reference.

It will be apparent, that the disclosed operating probe will be applicable to other operating sites in the body. In an application filed of even date herewith, I specify by location operation sites. These operating sites are all adjacent to constrained cavities having narrow substantially non manipulable entrance confines. These narrow substantially non manipulable entrance confines inhibit, retard and practically prevent appreciable side to side motion of a probe. That is to say, the probe can not be manipulated at its controlling end other than accommodating in, out and rotation. The whole surgical movement of the system has to occur at the distal end—and not by side-to-side motion of the probe at the controlling end.

Accordingly, the readers attention is invited to that application filed by myself, Michael I. Kulick, of even date herewith, entitled ENERGY DISCHARGING SURGICAL PROBE AND SURGICAL PROCESS HAVING DISTAL NON CONTACT ENERGY APPLICATION WITHOUT CONCOMITANT PROXIMAL MOVEMENT, U.S. Pat. application Ser. No. 07/646,948 filed Jan. 28, 1991. In that application I specify specific portal for surgical entry including specified portals in the hand, wrist, foot, mandibular joint, and the scar tissue interface between the female breast and an inserted breast implant.

It will be understood that this specification is exemplary and the invention herein to be liberally construed within the scope of the attached claims.

What is claimed is:

1. A process for surgery on the transverse carpal ligament of a hand comprising the steps of:
   providing a probe having a blunt non-dissecting tip, said probe defining a first interior conduit;
   providing means for defining a cavity behind said tip, said cavity having an opening, said blunt non-dissecting tip being adapted for insertion into the hand with said cavity opening disposed to the palmar side of the hand;

providing said first interior conduit of said probe with an optical viewing device, said optical viewing device protruding into said cavity for viewing of said cavity at the end of said probe;

providing a second conduit for conducting energy sufficient for the non-contact transection of the transverse carpal ligament, said second conduit protruding from said opening of said cavity at the end of said probe and terminating in the field of view of said viewing device for the discharge of said energy;

making an incision for inserting said probe into the hand;

inserting said probe into the hand within the carpal tunnel with said cavity behind said blunt non-dissecting tip being upwardly exposed underneath the transverse carpal ligament;

visualizing the transverse carpal ligament through said optical viewing device at said opening of said cavity;

supplying to said second conduit energy for transecting the transverse carpal ligament during said visualization step with the interface of the transecting being visible through the optical viewing device.

2. The process of claim 1 further including moving said second conduit with respect to said probe during said supplying of energy to said second conduit.

3. The process of claim 2 wherein said moving of said second conduit includes moving said second conduit in and out of said probe.

4. The process of claim 2 wherein said moving of said second conduit includes steering said second conduit with respect to said probe.

5. The process of claim 4 wherein said steering of said second conduit includes steering said second conduit side to side and up and down with respect to said probe.

6. The process of claim 1 wherein said optical viewing device is movable relative to said probe.

7. The process of claim 1 wherein said supplying of energy to said second conduit includes supply lasing energy to said second conduit.

8. The process of claim 1 further including:
providing said probe with a suction conduit and,
providing suction to said suction conduit.

9. The process of claim 1 wherein providing said means for defining a cavity includes:
providing said probe with a collapsible and expansible shield;
collapsing said shield with respect to said probe during said insertion of said probe into the hand; and,
expanding said shield during said supplying of energy to said second conduit.

10. The process of claim 9 wherein said shield is disposed between the contents of said carpal tunnel and said transverse carpal ligament when said probe is inserted into the hand.

11. The process of claim 9 wherein said providing of a collapsible shield further comprises:
providing a flexible mesh structure disposed about the exterior of said probe as said shield;
collapsing said flexible mesh structure about said probe during said insertion of said probe into the hand such that said collapsible mesh structure at least partially encloses said cavity and thereby defines a first cavity size; and,
expanding said flexible mesh structure to create an expanded second size of said cavity during said supplying of energy to said second conduit.

12. The process of claim 9 wherein said providing of a shield further comprises:
providing a balloon disposed about the exterior of said probe as said shield;
collapsing said balloon against said probe during said insertion of said probe into the hand; and,
expanding said balloon during said supplying of energy to said second conduit.

13. The process of claim 1 wherein said insertion of said probe into the hand includes inserting said probe proximate to the wrist adjacent the hand.

14. The process of claim 1 wherein said probe rotates.

15. The process of claim 1 further including providing a grasping device in said probe.

16. A process for surgery on the transverse carpal ligament of a hand comprising the steps of:
providing a probe having a blunt non-dissecting tip, said probe defining at least one interior conduit;
providing said probe with a cavity behind said tip for defining an operating interval behind said blunt non-dissecting tip, said cavity having an opening adapted to be disposed to the palmar side of the hand;
providing said at least one interior conduit of said probe with an optical viewing device, said optical viewing device protruding into said cavity;
providing a fiber for conducting laser energy sufficient for the non-penetrating transection of the transverse carpal ligament, said fiber being disposed within and protruding from the opening of said cavity at the end of said probe behind said blunt non-dissecting tip and terminating in the field of view of said viewing device for the discharge of said laser energy;
making an incision for inserting said probe into the hand;
inserting said probe into the hand within the carpal tunnel underneath the transverse carpal ligament with said blunt non-dissecting tip inserted into said incision followed by the remainder of said probe;
visualizing the transverse carpal ligament through said optical viewing device at said opening of said cavity;
supplying laser energy to said fiber for non-penetrating transecting of the transverse carpal ligament during said visualization with the interface of the transecting being visible through the optical viewing device step.

17. The process of claim 16 further including moving said fiber with respect to said probe during said supplying of laser energy to said fiber.

18. The process of claim 16 wherein said providing of said probe includes providing a semi rigid probe.

19. The process of claim 16 wherein said providing of said probe includes providing a rigid probe.

20. The process of claim 16 and further including steering said fiber side to side and up and down with respect to said probe.

21. The process of claim 16 further including:
providing said probe with a suction conduit; and,
providing suction to said suction conduit.

22. The process of claim 16 further including:
providing an expansible and collapsible shield to said probe;

collapsing said shield with respect to said probe during said insertion of said probe in the hand; and, expanding said shield during said supplying of laser energy to said fiber.

23. The process of claim 22 wherein said shield is disposed between the contents of said carpal tunnel and said transverse carpal ligament when said probe is inserted into the hand.

24. The process of claim 22 wherein said providing of said shield further comprises:

providing a flexible mesh structure disposed about the exterior of said probe as said shield;

collapsing said flexible mesh structure about said probe during said insertion of said probe in the hand such that said collapsible mesh structure at least partially encloses said cavity and thereby defines a first cavity size; and, expanding said flexible mesh structure to create an expanded second size of said cavity during said supplying of laser energy to said fiber.

25. The process of claim 22 wherein said providing of a shield further comprises:

providing a balloon disposed around the exterior of said probe as said shield;

collapsing said balloon to said probe during said insertion of said probe in the hand; and, expanding said balloon during said supplying of laser energy to said fiber.

26. The process of claim 22 wherein said insertion of said probe includes inserting said probe proximate to the wrist adjacent the hand.

27. A process for surgery on the transverse carpal ligament of the hand comprising the steps of:

providing a probe having a blunt non-dissecting tip, said probe defining a first interior conduit;

providing said probe, with a cavity behind said tip for providing upon insertion to said carpal tunnel an operating cavity, said cavity forming the distal end of said first interior conduit and including an opening adapted to face the palmar side of the hand;

providing said first interior conduit of said probe with an optical viewing device, said optical viewing device protruding into said cavity;

providing a second conduit for conducting energy sufficient for the non-penetrating transection of the transverse carpal ligament, said second conduit protruding from the opening at the end of said probe and terminating in the field of view of said viewing device for the discharge of said energy;

making an incision for inserting said probe into the hand;

inserting said probe into the hand within the carpal tunnel underneath the transverse carpal ligament with said blunt non-dissecting tip inserted first followed by the remainder of said probe;

providing a shield to said probe;

collapsing said shield with respect to said probe during said insertion of said probe into the hand;

visualizing the transverse carpal ligament through said optical viewing device at said cavity behind said blunt non-dissecting tip of said probe from the carpal tunnel to and toward the palmar side of the hand;

supplying said second conduit with energy for the non-penetrating transecting of the transverse carpal ligament during said visualization with the interface of the transecting being visible through the optical viewing device step; and expanding said shield during said supplying of said energy to said second conduit.

28. The process of claim 27 wherein said shield is disposed between the contents of said carpal tunnel and said transverse carpal ligament when the probe is inserted into the hand.

29. The process of claim 27 wherein said providing of said shield further comprises:

providing a flexible mesh structure disposed about the exterior of said probe as said shield;

collapsing said flexible mesh structure about said probe during said insertion of said probe into the hand such that said collapsible mesh structure at least partially encloses said cavity and thereby defines a first cavity size; and, expanding said flexible mesh structure to create an expanded second size of said cavity about said probe during said supplying of energy to said second conduit.

30. The process of claim 27 wherein said providing of said shield further comprises:

providing a balloon disposed about the exterior of said probe as said shield;

collapsing said balloon to said probe during said insertion of said probe into the hand; and, expanding said balloon during said supplying of energy to said second conduit.

31. A process for surgery on an operating site adjacent to constrained surfaces having narrow substantially non-compressible entrance confines with structure to be differentiated within a constrained cavity within the human anatomy comprising the steps of:

providing a probe defining a first interior conduit having an opening, said probe being adapted for insertion into a constrained area adjacent said surfaces along said narrow, substantially non-compressible entrance confines with said opening disposed to an operating site within said constrained area adjacent said surface;

providing a blunt non-dissecting tip to said probe;

providing a cavity behind said tip wherein said cavity is aligned with said opening for providing at said tip an interval for exposing said operating site;

providing said first interior conduit of said probe with an optical viewing device, said optical viewing device protruding into said cavity for viewing of said operating site at the end of said probe;

providing a second conduit for conducting energy sufficient for the non-penetrating transection, incision or treatment of the anatomy of said operating site adjacent said constrained area, said second conduit protruding from the opening of said interior conduit and terminating in the field of view of said viewing device for the discharge of said energy;

making an incision overlying said narrow, substantially non-compressible entrance confines for inserting said probe into the constrained area adjacent said surfaces;

inserting said probe into the constrained area along said narrow, substantially non-compressible entrance confines with said blunt non-dissecting tip leading said probe during said inserting;

visualizing the operating site through said optical viewing device;

supplying said second conduit with energy for transecting, incising or treating the operating site during said visualization step with the interface of cutting visible to the optic viewing device.

32. The process of claim 31 wherein said constrained area is selected from a group of cavities consisting of: portals in the hand, elbow, wrist, foot, ankle, temporomandibular joint, and the scar tissue interface between the female breast and an inserted breast implant.

33. The process of claim 31 further including moving said second conduit with respect to said probe during said supplying of energy to said second conduit.

34. The process of claim 33 wherein said moving of said second conduit includes moving said second conduit in and out of said probe.

35. The process of claim 33 wherein said moving of said second conduit includes steering said second conduit with respect to said probe.

36. The process of claim 35 wherein said steering of said second conduit includes steering said conduit side to side and up and down with respect to said probe.

37. The process of claim 31 wherein said supplying of energy to said second conduit includes supply lasing energy to said second conduit.

38. The process of claim 31 further including:
providing said probe with a suction conduit; and,
providing suction to said suction conduit.

39. The process of claim 31 further including the steps of:
providing a collapsible and expansible shield to said probe;
collapsing said shield with respect to said probe during said insertion of said probe into the constrained area; and,
expanding said shield during said supplying of energy to said second conduit.

40. The process of claim 31 further including the steps of providing a grasping device at the distal end of said probe; and
grasping a portion of the anatomy during said supplying of energy to said second conduit.

41. The process of claim 39 wherein said constrained area is the carpal tunnel and said shield is disposed between the contents of said carpal tunnel and said transverse carpal ligament when said probe is inserted into said constrained area.

42. The process of claim 41 wherein said providing of said shield further comprises:
providing a flexible mesh structure disposed about the exterior of said probe as said shield;
collapsing said flexible mesh structure about said probe during said insertion of said probe into said constrained area such that said shield at least partially encloses said cavity and thereby defines a first cavity size; and,
expanding said flexible mesh structure to create an expanded second size of said cavity during said supplying of energy to said second conduit.

43. The process of claim 41 wherein said providing of said collapsible shield further comprises:
providing a balloon disposed about the exterior of said probe as said shield;
collapsing said balloon to said probe during said insertion of said probe into said constrained area; and,
expanding said balloon during said supplying of energy to said second conduit.

44. The process of claim 31 wherein said insertion of said probe further includes inserting said probe proximate to a wrist of a patient.

* * * * *